(12) United States Patent
Kahre et al.

(10) Patent No.: US 6,616,706 B1
(45) Date of Patent: Sep. 9, 2003

(54) METHOD FOR PRODUCING HAIR DYE PRODUCTS

(75) Inventors: Joerg Kahre, Leichlingen (DE); Peter Busch, Erkrath (DE); Thomas Foerster, Erkrath (DE); Hermann Hensen, Haan (DE); Holger Tesmann, Juechen (DE); Markus Sumser, Herne (DE); Adrian Pitfield, Brombachtal (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/423,507

(22) PCT Filed: May 2, 1998

(86) PCT No.: PCT/EP98/02595

§ 371 (c)(1),
(2), (4) Date: Jan. 21, 2000

(87) PCT Pub. No.: WO98/51267

PCT Pub. Date: Nov. 19, 1998

(30) Foreign Application Priority Data

May 12, 1997 (DE) .......... 197 19 504

(51) Int. Cl.⁷ .............. A61K 7/13
(52) U.S. Cl. ......... 8/405; 8/405; 8/406; 8/435; 8/580; 8/606; 8/901; 8/907; 424/62; 424/70.6; 424/70.28
(58) Field of Search ........... 8/405, 406, 435, 8/580, 606, 901, 907, 909; 424/62, 70.6, 70.28

(56) References Cited

U.S. PATENT DOCUMENTS

| | | | | |
|---|---|---|---|---|
| 3,811,830 A | * | 5/1974 | DeMarco ............... | 8/405 |
| 4,172,887 A | | 10/1979 | Vanlerberghe et al. ....... | 424/70 |
| 4,927,627 A | * | 5/1990 | Schrader et al. ............ | 423/62 |
| 5,021,066 A | | 6/1991 | Abey et al. .............. | 8/408 |
| 5,221,286 A | * | 6/1993 | Singleton et al. .......... | 8/405 |
| 5,279,818 A | * | 1/1994 | Halloran et al. ........... | 424/71 |
| 5,298,240 A | | 3/1994 | Schroeder et al. .......... | 424/70 |
| 5,300,285 A | * | 4/1994 | Holloran et al. ........... | 424/71 |
| 5,374,716 A | | 12/1994 | Biemann et al. .......... | 536/18.6 |
| 5,480,459 A | * | 1/1996 | Mager et al. ............. | 8/408 |
| 5,576,425 A | | 11/1996 | Hill et al. ............... | 536/18.6 |
| 5,656,280 A | * | 8/1997 | Herb et al. ............... | 8/405 |
| 5,716,418 A | * | 2/1998 | Matzik et al. ............. | 8/406 |
| 5,718,891 A | | 2/1998 | Prat et al. .............. | 424/70.28 |
| 5,817,155 A | * | 10/1998 | Yasuda et al. ............. | 8/405 |
| 5,840,943 A | | 11/1998 | Ansmann et al. .......... | 554/166 |
| 5,998,354 A | * | 12/1999 | Turowski-Wanke et al. ..... | 510/416 |

FOREIGN PATENT DOCUMENTS

| | | |
|---|---|---|
| DE | 11 65 574 | 3/1964 |
| DE | 38 19 193 | 12/1989 |
| DE | 283027 | * 10/1990 |
| DE | 40 10 393 | 10/1991 |
| DE | 41 40 562 | 6/1993 |
| DE | 43 08 794 | 4/1994 |
| DE | 43 18 171 | 12/1994 |
| DE | 43 37 041 | 5/1995 |
| DE | 44 11 557 | 10/1995 |
| EP | 0 301 298 | 2/1989 |
| EP | 0 490 053 | 6/1992 |
| EP | 0 820 758 | 1/1998 |
| FR | 2 252 840 | 12/1978 |
| GB | 962 919 | 7/1994 |
| WO | WO90/03977 | 4/1990 |
| WO | WO91/01295 | 2/1991 |
| WO | WO94/20241 | 9/1994 |
| WO | WO95/34528 | 12/1995 |

OTHER PUBLICATIONS

Mar. 1997, Abstract No. 028, vol. 395, Research Disclosure.*

* cited by examiner

Primary Examiner—Mark Kopec
Assistant Examiner—Eisa Elhilo
(74) Attorney, Agent, or Firm—John E. Drach; Steven J. Trzaska

(57) ABSTRACT

A process for making a hair colorant composition involving: (a) providing a phase inversion temperature emulsion or microemulsion containing: (i) an oil component; and (ii) an emusifier selected from the group consisting of an alkyl and/or alkenyl oligoglycoside, an anionic surfactant, an esterquat, a polyolpoly-12-hydroxystearate, a fatty alcohol, a fatty alcohol polyethylene glycol ether, and mixtures thereof; (b) providing a dye component; and (c) combining (a) and (b) at a temperature of from 15 to 25° C.

16 Claims, No Drawings

METHOD FOR PRODUCING HAIR DYE PRODUCTS

BACKGROUND OF THE INVENTION

This invention relates to a process for the production of hair colorants in which a PIT or microemulsion is initially prepared and the dyes are stirred cold into the resulting PIT or microemulsion.

Emulsion-based hair colorants are very largely produced by hot processes, i.e. temperatures above 60° C. and preferably above 80° C. have to be used for the production of stable products. Thereafter, the emulsions are slowly cooled which leads to very considerable reactor possession times. It will readily be appreciated that any process which would enable the colorants to be produced as it were in the cold would have significant economic advantages.

Accordingly, the problem addressed by the present invention was to provide such a process.

DESCRIPTION OF THE INVENTION

The present invention relates to a process for the production of hair colorants in which an aqueous preparation in the form of a PIT emulsion or microemulsion is initially prepared using oil components and emulsifiers selected from the group consisting of alkyl and/or alkenyl oligoglycosides, anionic surfactants, esterquats, polyolpoly-12-hydroxystearates, fatty alcohols and fatty alcohol polyethylene glycol ethers and the dyes or rather secondary and primary intermediates are stirred into the resulting PIT emulsion or microemulsion in a cold process.

It has surprisingly been found that dyes can also be incorporated cold in PIT or microemulsions prepared using selected emulsifiers so that the production times can be significantly shortened. The PIT or microemulsions used may contain all the necessary components except for the dyes. In the most simple case, however, they may also consist solely of oil components, emulsifiers and optionally other heat-stable additives, so that more sensitive components, such as protein derivatives or perfume oils for example, can then be incorporated cold together with the dyes.

Oil Components

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more especially 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, ring-opening products of epoxidized fatty acid esters with polyols, silicone oils and/or aliphatic or naphthenic hydrocarbons.

Emulsifiers

Suitable emulsifiers for the production of the PIT or microemulsion are alkyl and/or alkenyl oligoglucosides, anionic surfactants, esterquats, polyolpoly-12-hydroxystearates, fatty acid esters, fatty alcohols and fatty alcohol polyethylene glycol ethers and mixtures thereof.

Alkyl and alkenyl oligoglycosides are known nonionic surfactants corresponding to formula (I):

$$R^1O\text{-}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.

Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Alkyl ether sulfates based on adducts of 1 to 10 mol of ethylene oxide with fatty alcohols containing 8 to 22 and preferably 12 to 18 carbon atoms in the form of their sodium or magnesium salts are preferably used.

Esterquats are generally understood to be quaternized fatty acid triethanolamine ester salts. These are known substances which may be obtained by the relevant methods of preparative organic chemistry, cf. International patent application WO 91/01295 (Henkel). According to this document, triethanolamine is partly esterified with fatty acids in the presence of hypophosphorous acid, air is passed through and the reaction product is quaternized with dimethyl sulfate or ethylene oxide. In addition, a process for the production of esterquats, in which the quaternization of triethanolamine esters is carried out in the presence of suitable dispersants, preferably fatty alcohols, is known from DE-C1 4307894 (Henkel). Overviews on this subject have been published, for example, by R. Puchta et al. in Tens. Surf. Det., 30, 186 (1993), by M. Brock in Tens. Surf, Det. 30, 394 (1993), by R. Lagerman et al. in J. Am. Oil. Chem. Soc., 71, 97 (1994) and by I. Shapiro in Cosm. Toil. 109, 77 (1994). The quaternized fatty acid triethanolamine ester salts correspond to formula (II):

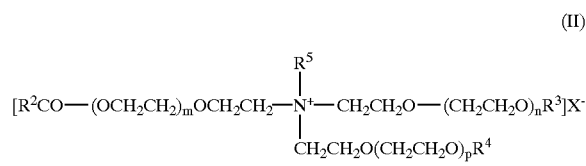

(II)

in which $R^2CO$ is an acyl group containing 6 to 22 carbon atoms, $R^3$ and $R^4$ independently of one another represent hydrogen or have the same meaning as $R^2CO$, $R^5$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained for example in the pressure hydrolysis of natural fats and oils. Technical $C_{12/18}$ cocofatty acids and, in particular, partly hydrogenated $C_{16/18}$ tallow or palm oil fatty acids and high-elaidic $C_{16/18}$ fatty acid cuts are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{12/18}$ tallow or palm oil fatty acid (iodine value 0 to 40). In performance terms, quaternized fatty acid triethanolamine ester salts corresponding to formula (I), in which $R^2CO$ is an acyl group containing 16 to 18 carbon atoms, $R^3$ has the same meaning as $R^2CO$, $R^4$ is hydrogen, $R^5$ is a methyl group, m, n and p stand for 0 and X stands for methyl sulfate, have proved to be particularly advantageous.

Other suitable esterquats besides the quaternized fatty acid triethanolamine ester salts are quaternized ester salts of fatty acids with diethanolalkyamines corresponding to formula (III):

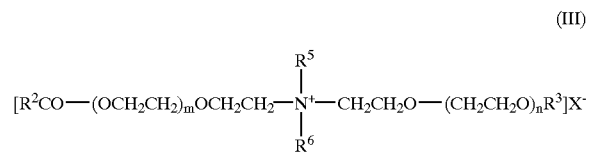

(III)

in which $R^2CO$ is an acyl group containing 6 to 22 carbon atoms, $R^3$ is hydrogen or has the same meaning as $R^2CO$, $R^5$ and $R^6$ independently of one another are alkyl groups containing 1 to 4 carbon atoms, m and n together stand for 0 or numbers of 1 to 12 and X stands for halide, alkyl sulfate or alkyl phosphate.

Finally, another group of suitable esterquats are the quaternized ester salts of fatty acids with 1,2-dihydroxypropyl dialkylamines corresponding to formula (IV):

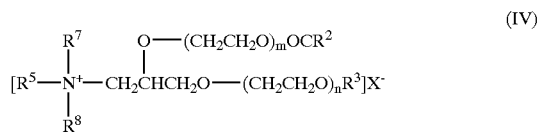

(IV)

in which $R^2CO$ is an acyl group containing 6 to 22 carbon atoms, $R^2$ is hydrogen or has the same meaning as $R^2CO$, $R^5$, $R^7$ and $R^8$ independently of one another are alkyl groups containing 1 to 4 carbon atoms, m and n together stand for 0 or numbers of 1 to 12 and X stands for halide, alkyl sulfate or alkyl phosphate. So far the choice of the optimum degree of esterification is concerned, the examples mentioned in regard to (II) also apply to the esterquats of formulae (III) and (IV).

The polyolpoly-12-hydroxystearates are known compounds which are marketed by Henkel KGaA, Düsseldorf, FRG, for example under the registered names of "Dehymuls® PGPH" and "Eumulgin® VL 75" (a mixture of Coco Glucosides in a ratio by weight of 1:1, cf. also International patent application WO 95/34528 (Henkel). The polyol component of the emulsifiers may be derived from compounds which contain at least 3, preferably 3 to 12 and more preferably 3 to 8 hydroxyl groups and 2 to 12 carbon atoms. Typical examples are:

(a) glycerol and polyglycerol;

(b) alkylene glycols such as, for example, ethylene glycol, diethylene glycol, propylene glycol;

(c) methylol compounds such as, in particular, trimethylol ethane, tri-methylol propane, trimethylol butane, pentaerythritol and dipentaerythritol;

(d) alkyl oligoglucosides containing 1 to 22 carbon atoms, preferably 1 to 8 carbon atoms and more preferably 1 to 4 carbon atoms in the alkyl moiety, such as, for example methyl and butyl glucoside;

(e) sugar alcohols containing 5 to 12 carbon atoms, such as sorbitol or mannitol for example;

(f) sugars containing 5 to 12 carbon atoms, such as glucose or sucrose for example;

(g) amino sugars, such as glucamine for example.

Among the emulsifiers to be used in accordance with the invention, particular significance is attributed to reaction products based on polyglycerol by virtue of their excellent performance properties. It has proved to be of particular advantage to use selected polyglycerols with the following homolog distribution (the preferred ranges are shown in brackets):

| | |
|---|---|
| Glycerol | 5 to 35 (15 to 30) % by weight |
| Diglycerols | 15 to 40 (20 to 32) % by weight |
| Triglycerols | 10 to 35 (15 to 25) % by weight |
| Tetraglycerols | 5 to 20 (8 to 15) % by weight |
| Pentaglycerols | 2 to 10 (3 to 8) % by weight |
| Oligoglycerols | to 100% by weight |

Fatty alcohols and fatty alcohol polyethylene glycol ethers, which may also be used as emulsifiers, preferably correspond to formula (V):

$$R^9O(CH_2CH_2O)_nH \qquad (V)$$

in which $R^9$ is a linear or branched alkyl and/or alkenyl group containing 12 to 22 and preferably 16 to 18 carbon atoms and n is 0 or a number of 1 to 25. Typical examples are lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof and adducts thereof with 1 to 25 and preferably 10 to 20 mol of ethylene oxide. A particularly preferred embodiment is characterized by the use of cetyl alcohol, stearyl alcohol, cetearyl alcohol and products of the addition of 10 to 20 mol of ethylene oxide with cetearyl alcohol.

PIT and Microemulsions

In one preferred method of production, so-called PIT emulsions are prepared by heating the oil components and the emulsifiers to the production temperature and mixing them with the necessary quantity of water which has also been heated to the production temperature. The production temperature should be above the phase inversion temperature range. Accordingly, this temperature range should first be determined using a sample mixture. All the components of the emulsion, including the water, are heated, the temperature range in which conductivity undergoes a drastic reduction through phase reversal being determined by means of a conductivity measuring instrument. An overview of PIT emulsions was published by A. Wadle et al. in Parf. Kosm. 72 250 (1996). DE-A1 3819193, DE-A1 4010393, DE-A1 4140562, DE-A1 4318171 and DE-A1 4337041 (Henkel) are cited as representative of the extensive prior art literature available on the subject of PIT emulsions.

Instead of the PIT emulsions, so-called microemulsions can also be prepared using the oil components and selected emulsifiers. Microemulsions are optically isotropic thermodynamically stable systems which contain a water-insoluble oil component, emulsifiers—preferably alkyl glucosides—and water. The clear or transparent appearance of the microemulsions is attributable to the small particle size of the dispersed emulsion droplets which is largely below 100 nm and, on average, always below 50- nm. Overviews of the production and use of microemulsions have been published by H. Eicke in SÖFW Journal, 118, 311 (1992) and by Th. Förster et al. in SÖFW Journal 122, 746 (1996); reference is also made in this connection to DE-A1 4411557 (Henkel) and EP-A1 0687206 (L'Oréal).

The PIT or microemulsions may contain the oil components in quantities of 10 to 90% by weight and preferably 20 to 50% by weight and the emulsifiers in quantities of 1 to 20% by weight and preferably 5 to 15% by weight, based on the emulsions.

Dyes

In the process according to the invention, the dyes are stirred in cold after the preparation of the PIT or microemulsion. Suitable dyes are, for example, substantive dyes, for example from the group of nitro-phenylenediamines, nitroaminophenols, anthraquinones and indophenols, such as for example the compounds known under the International names or trade names of HC Yellow 2, HC Yellow 4, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16, Basic Brown 17, pricramic acid and Rodol 9 R and also 4-amino-2-nitrodiphenylamine-2'-carboxylic acid, 6-nitro-1,2,3,4-tetrahydroquinoxaline, (N-2,3-dihydroxypropyl-2-nitro4-tri-fluoromethyl)-aminobenzene and 4-N-ethyl-1,4-bis-(2'-hydroxyethylamino)-2-nitrobenzene hydrochloride. Naturally occurring dyes such as, for example, henna red, henna neutral, henna black, camomile blossom, sandalwood, black tea, black alder bark, sage, logwood, madder root, catechu, sedre and alkanet may also be added to the emulsions.

Besides substantive dyes, oxidation dyes consisting of primary and secondary intermediates may also be added to the emulsions. The primary intermediates used are, for example, primary aromatic amines containing another free or substituted hydroxy or amino group in the para or ortho position, diaminopyridine derivatives, heterocyclic hydrazones, 4-amino-pyrazolone derivatives and 2,4,5,6-tetraaminopyrimidine and derivatives thereof. Special representatives are inter alia p-toluylenediamine, p-aminophenol, N,N-bis-(2-hydroxyethyl)-p-phenylenediamine, 2-(2,5-diamino-phenoxy)-ethanol, 1-phenyl-3-carboxyamido-4-amino-5-pyrazolone and 4-amino-3-methylphenol, 2-(2-hydroxyethyl)-1,4-aminobenzene and 2,4,5,6-tetraaminpyrimidine. The secondary intermediates used are generally m-phenylenediamine derivatives, naphthols, resorcinol and resorcinol derivatives, pyrazolones, m-aminophenols and pyridine derivatives. Particularly suitable secondary intermediates are 1-naphthol, pyrogallol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diamino-phenoxy)-propane, 2-chlororesorcinol, 2-chloro-6-methyl-3-aminophenol, 2-methyl resorcinol, 2,5-dimethyl resorcinol, 2,6-dihydroxypyridine and 2,6-diaminopyridine.

So far as other dye components are concerned, reference is specifically made to the Colipa-Liste published by the Industrieverband Körperflege und Waschmittel, Frankfurt. The dyes may be added to the emulsions in quantities of 0.1 to 10% by weight and preferably in quantities of 1 to 5% by weight, based on the emulsions. In the context of the invention, cold stirring is understood to be mixing at ambient temperature, i.e. in the range from 15 to 25° C.

Auxiliaries and Additives

In the context of the process according to the invention, the emulsions may contain other auxiliaries and additives such as, for example, co-emulsifiers, superfatting agents, stabilizers, waxes, consistency factors, thickeners, cationic polymers, silicone compounds, biogenic agents, antidandruff agents, film formers, preservatives, hydrotropes, solubilizers or perfume oils.

Typical examples of suitable mild, i.e. particularly dermatologically compatible, surfactants are fatty alcohol polyglycol ether sulfates, monoglyceride sulfates, monoand/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkyl (ether) phosphates, alkyl amidobetaines and/or protein fatty acid condensates (preferably based on wheat proteins).

Suitable co-emulsifiers are, for example, nonionic surfactants from at least one of the following groups:

(1) $C_{12/18}$ fatty acid monoesters and diesters of products of the addition of 1 to 30 mol of ethylene oxide onto glycerol;
(2) glycerol monoesters and diesters and sorbitan monoesters and diesters of saturated and unsaturated fatty acids containing 6 to 22 carbon atoms and ethylene oxide adducts thereof;
(3) adducts of 15 to 60 mol of ethylene oxide with castor oil and/or hydrogenated castor oil;
(4) products of the addition of 2 to 15 mol of ethylene oxide onto castor oil and/or hydrogenated castor oil;
(5) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(6) trialkyl phosphates and mono-, di- and/or tri-PEG-alkyl phosphates;
(7) wool wax alcohols;
(8) polysiloxane/polyalkyl polyether copolymers and corresponding derivatives;
(9) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol, and
(10) polyalkylene glycols.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a C8/18 alkyl or acyl group, contain at least one free amino group and at least one —COOH—or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency factors mainly used are fatty alcohols containing 12 to 22 and preferably 16 to 18 carbon atoms and also partial glycerides. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethyl-aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. In the context of the invention, biogenic agents are, for example, tocopherol, tocopherol acetate, tocopherol palmitate, ascorbic acid, retinol, bisabolol, allantoin, phytantriol, panthenol, AHA acids, amino acids, ceramides, pseudoceramides, essential oils, plant extracts and vitamin complexes. Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases include colloidal silica, layer silicates, such as montmorillonite, clays minerals, Pemulen and alkyl-modified Carbopol types (Goodrich). Suitable preservatives are, for example, phenoxyethanol, formaldehyde solution, parabens, pentanediol or sorbic acid. Ammonia, amines or basic amino acids are suitable for pH adjustment.

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable perfume oils include the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Suitable synthetic or semisynthetic perfume oils are Ambroxan, eugenol, isoeugenol, citronellal, hydroxycitronellal, geranoil, citronellol, geranyl acetate, citral, ionone and methyl ionone.

It is immaterial whether the auxiliaries and additives are added during the preparation of the PIT or microemulsion or at a later stage. The cold-produced emulsion containing the dye may then be diluted to the in-use concentration and, if necessary, contacted with a corresponding hydrogen-peroxide-containing emulsion which may be produced similarly to the PIT or microemulsion.

EXAMPLES

Example 1

An emulsion containing 33.3 g of Emulgade® CM [Cetyl Isononanoate (and) Ceteareth-20 (and) Cetearyl Alcohol (and) Glyceryl Stearate (and) Glycerin (and) Cetyl Palmitate (and) Ceteareth-12, Henkel KGaA, Düsseldorf, DE], 9 g of $C_{8/18}$ alkyl glucoside, 9 g of colloidal silica, 3 g of ammonium chloride, aqueous ammonia solution to 100 g (pH=10.5) was prepared by the PIT method. 7.5 mmol of a primary intermediate (N,N'-bis-(4-aminophenyl)-piperidine) and 7.5 mmol of a secondary intermediate (resorcinol) were then stirred into the PIT emulsion at 20° C. The oxidative development was then carried out with hydrogen peroxide. The hair color obtained was dark blond.

Example 2

A PIT emulsion containing 33.3 g of Lamesoft® PW 45 [Cetyl Palmitate (and) Hydrogenated Castor Oil (and) Glyceryl Stearate (and) Beheneth-10; Henkel KGaA], 9 g of $C_{8/18}$ alkyl glucoside, 9 g of colloidal silica, 3 g of ammonium chloride, aqueous ammonia solution to 100 g (pH=10.5) was prepared as described in Example 1. 7.5 mmol of 2,4,5,6-tetraaminopyridine and 2,6-bis-(2-hydroxyethylamino)-toluene were then stirred into the PIT emulsion at 20° C. The oxidative development was again carried out with hydrogen peroxide. The hair color obtained was deep red.

Examples 3 to 15

The following hair coloring cream emulsion was then prepared cold on the basis of these Examples (water to 100% by weight):

| | |
|---|---|
| cream base according to Example 1 or 2 | 50.0% by weight |
| primary intermediate | 7.5 mmol |
| secondary intermediate | 7.5 mmol |
| $Na_2SO_3$ (inhibitor) | 1.0% by weight |
| $(NH_4)_2SO_4$ | 1.0% by weight |
| conc. ammonia | to pH 10 |

The constituents were mixed together in the order listed. After addition of the oxidation dye precursors and the inhibitor, the pH value of the emulsion was first adjusted to 10 with concentrated ammonia solution, after which the emulsion was made up with water to 100 g. The color was oxidatively developed with hydrogen peroxide solution as the oxidizing solution. To this end, 50 g of hydrogen peroxide solution (1, 3 or 9%) were added to and mixed with the emulsion. The coloring cream was applied to ca. 5 cm long tresses of standardized, 90% grey but not specially pretreated human hair and left thereon for 30 minutes at 32° C. After the coloring process, the hair was rinsed, washed with a normal shampoo and then dried. The colors listed in Table 1 were obtained:

TABLE 1

| | Colors | | | |
|---|---|---|---|---|
| Primary intermediate | Secondary intermediate | Substantive dye | c[$H_2O_2$] | Shade |
| 2,6-Bis(2-hydroxyethylamino)toluene | 2,4,5,6-Tetraaminopyrimidine | — | 3 | Deep red |
| 2,6-Bis(2-hydroxyethylamino)toluene | 4-Hydroxy-2,5,6-triaminopyrimidine | — | 3 | Madder red |
| 2,6-Bis(2-hydroxyethylamino)toluene | 2-Dimethylamino-4,5,6-triaminopyrimidine | — | 3 | Brown-red |
| 2,6-Bis(2-hydroxyethylamino)toluene | 2-Methylamino-4,5,6-triaminopyrimidine | — | 3 | Red |
| 2,6-Bis(2-hydroxyethylamino)toluene | 2-Piperidyl-4,5,6-triaminopyrimidine | — | 3 | Madder red |
| 2,6-Bis(2-hydroxyethylamino)toluene | 2-Morpholino-4,5,6-triaminopyrimidine | — | 3 | Madder red |
| 2-Morpholino-4,5,6-triamino-pyrimidine + 2,7-dihydroxynaphthalene | 2,4,5,6-Tetraaminopyrimidine | — | 3 | Copper red |
| 2,6-Bis(2-hydroxyethylamino)toluene | 2-(2-Hydroxyethyl)-1,4-diaminobenzene | — | 1 | Violet |
| 2,6-Bis(2-hydroxyethylamino)toluene | 2-(2-Hydroxyethyl)-1,4-diaminobenzene | — | 9 | Violet |
| 2,6-Bis(2-hydroxyethylamino)toluene | 2,4,5,6-Tetraaminopyrimidine + 2,5-diaminotoluene | — | 1 | Grey-ruby |
| 2,6-Bis(2-hydroxyethylamino)toluene | 2,4,5,6-Tetraaminpyrimidine + diaminotoluene | — | 9 | Deep magenta |
| 2,6-Bis(2-hydroxyethylamino)toluene | 2-Dimethylamino-4,5,6-triaminopyrimidine | 4-(3'-Trimethylammoniumphenylazo)-1-phenyl-3-methyl-pyrazolone chloride | 1 | Cinnabar |
| 2,6-Bis(2-hydroxyethylamino)toluene | 2-Dimethylamino-4,5,6-triaminopyrimidine | 4-(3'-Trimethylammoniumphenylazo)-1-phenyl-3-methyl-pyrazolone chloride | 9 | Orange red |

What is claimed is:

1. A process for making a hair colorant composition comprising:

(a) providing a phase inversion temperature emulsion or microemulsion containing:
(i) an oil component; and
(ii) an emulsifier selected from the group consisting of an alkyl and/or alkenyl oligoglycoside, an anionic surfactant, an esterquat, a polyolpoly-12-hydroxystearate, a fatty alcohol, a fatty alcohol polyethylene glycol ether, and mixtures thereof;

(b) providing a dye component; and (c) combining (a) and (b) at a temperature of from 15 to 25° C.

2. The process of claim 1 wherein the emulsifier is the alkyl and alkenyl oligoglycoside corresponding to formula (I):

wherein $R^1$ is an alkyl and/or alkenyl radical containing from 4 to 22 carbon atoms, G is a sugar unit containing 5 or 6 carbon atoms, and p is a number from 1 to 10.

3. The process of claim 1 wherein the emulsifier is an alkyl ether sulfate.

4. The process of claim 1 wherein the emulsifier is an esterquat corresponding to formula (II):

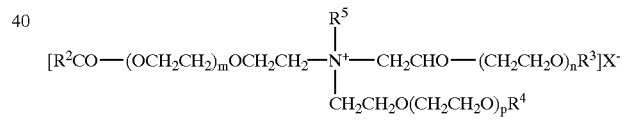

wherein $R^2CO$ is an acyl group containing from 6 to 22 carbon atoms, $R^3$ and $R^4$, independently of one another, represent hydrogen or have the same meaning as $R^2CO$, $R^5$ is an alkyl group containing from 1 to 4 carbon atoms or a $(CH_2CH_2O)_qH$ group, m, n and p together stand for a number up to 12, q is a number from 1 to 12 and X is a halide, alkyl sulfate or alkyl phosphate.

5. The process of claim 1 wherein the emulsifier is an esterquat corresponding to formula (III):

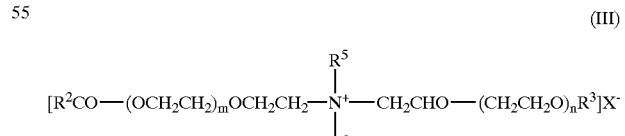

wherein $R^2CO$ is an acyl group containing from 6 to 22 carbon atoms, $R^3$ is hydrogen or has the same meaning as $R^2CO$, $R^5$ and $R^6$, independently of one another, represent an alkyl group containing from 1 to 4 carbon atoms, m and n together stand for a number up to 12, and X is a halide, alkyl sulfate or alkyl phosphate.

6. The process of claim 1 wherein the emulsifier is an esterquat corresponding to formula (IV):

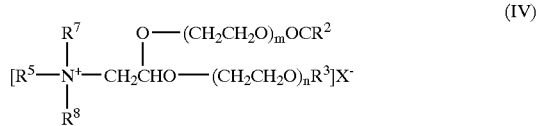 (IV)

wherein $R^2CO$ is an acyl group containing from 6 to 22 carbon atoms, $R^3$ is hydrogen or has the same meaning as $R^2CO$, $R^5$, $R^7$ and $R^8$, independently of one another, represent an alkyl group containing from 1 to 4 carbon atoms, m and n together stand for a number up to 12, and X is a halide, alkyl sulfate or alkyl phosphate.

7. The process of claim 1 wherein the emulsifier is a polyglycerol poly-12-hydroxystearate.

8. The process of claim 1 wherein the emulsifier is a fatty alcohol and/or fatty alcohol polyethylene glycol ether corresponding to formula (VI):

$$R^9O(CH_2CH_2O)_nH \qquad (VI)$$

wherein $R^9$ is a linear or branched alkyl and/or alkenyl group containing from 12 to 22 carbon atoms, and n is a number up to 25.

9. The process of claim 1 wherein the oil component is present in the emulsion in an amount of from 10 to 90% by weight, based on the weight of the emulsion.

10. The process of claim 1 wherein the oil component is present in the emulsion in an amount of from 20 to 50% by weight, based on the weight of the emulsion.

11. The process of claim 1 wherein the emulsifier is present in the composition in an amount of from 1 to 20% by weight, based on the weight of the emulsion.

12. The process of claim 1 wherein the emulsifier is present in the composition in an amount of from 5 to 15% by weight, based on the weight of the emulsion.

13. The process of claim 1 wherein the dye is present in the emulsion in an amount of from 0.1 to 10% by weight, based on the weight of the emulsion.

14. The process of claim 1 wherein the dye is present in the emulsion in an amount of from 1 to 5% by weight, based on the weight of the emulsion.

15. The process of claim 1 wherein the dye is selected from the group consisting of a substantive dye, an oxidation dye, and mixtures thereof.

16. The process of claim 1 wherein the emulsion further comprises an additive selected from the group consisting of a co-emulsifier, a superfatting agent, a stabilizer, a wax, a consistency factor, a thickener, a cationic polymer, a silicone compound, a biogenic agent, an antidandruff agent, a film former, a preservative, a hydrotrope, a solubilizer, a perfume oil, and mixtures thereof.

* * * * *